(12) United States Patent
Krzysik et al.

(10) Patent No.: US 6,534,074 B2
(45) Date of Patent: *Mar. 18, 2003

(54) ABSORBENT ARTICLES PROVIDING SKIN HEALTH BENEFITS

(75) Inventors: Duane Gerard Krzysik, Appleton, WI (US); David Roland Otts, Appleton, WI (US); Beth Anne Lange, Appleton, WI (US); Brenda Marie Nelson, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 17 days.

This patent is subject to a terminal disclaimer.

(21) Appl. No.: 09/779,819

(22) Filed: Feb. 8, 2001

(65) Prior Publication Data

US 2001/0014350 A1 Aug. 16, 2001

Related U.S. Application Data

(63) Continuation of application No. 09/379,928, filed on Aug. 24, 1999, now Pat. No. 6,287,581.

(51) Int. Cl.[7] .......................... A01N 25/34; A61F 13/00; A61F 13/15
(52) U.S. Cl. ....................... 424/402; 424/443; 514/847; 514/865; 604/304; 604/358
(58) Field of Search ................................ 424/443, 402, 424/400

(56) References Cited

U.S. PATENT DOCUMENTS

| | | |
|---|---|---|
| 3,896,807 A | 7/1975 | Buchalter |
| 4,100,324 A | 7/1978 | Anderson et al. |
| 4,273,786 A | 6/1981 | Kraskin |
| 4,381,782 A | 5/1983 | Mazurak et al. |
| 4,478,853 A | 10/1984 | Chaussee |
| 4,559,157 A | 12/1985 | Smith et al. |
| 4,604,281 A | 8/1986 | Deckner et al. |
| 4,690,821 A | 9/1987 | Smith et al. |
| 4,704,116 A | 11/1987 | Enloe |
| 4,798,603 A | 1/1989 | Meyer et al. |
| 4,818,464 A | 4/1989 | Lau |
| 4,842,593 A | 6/1989 | Jordan et al. |
| 4,846,823 A | 7/1989 | Enloe |
| 4,904,524 A | 2/1990 | Yoh |
| 5,019,073 A | 5/1991 | Roessler et al. |
| 5,079,003 A | 1/1992 | Scaffidi |
| 5,160,739 A | 11/1992 | Kanga |
| 5,176,671 A | 1/1993 | Roessler et al. |

(List continued on next page.)

FOREIGN PATENT DOCUMENTS

| | | |
|---|---|---|
| FR | 2 331 980 A1 | 6/1977 |
| GB | 880276 A | 10/1961 |
| JP | 59-227816 A | 12/1984 |

(List continued on next page.)

OTHER PUBLICATIONS

Wilkinson, J.B. et al., Editors, *Harry's Cosmeticology*, Seventh Edition, Chemical Publishing, New York, 1982, pp. 54–67.

(List continued on next page.)

Primary Examiner—Thurman K. Page
Assistant Examiner—Isis Ghali
(74) Attorney, Agent, or Firm—Patricia A. Charlier

(57) ABSTRACT

A superior skin barrier enhancing body facing material, such as a body side liner on an absorbent article, can be made by applying, on the outer surface of the body facing material, a lipid-enriched hydrophobic composition comprising a natural fat or oil, a sterol or sterol derivative, an emulsifying surfactant, a humectant, an emollient, a wax, and a viscosity enhancer, and thereafter resolidifying the composition to form a distribution of solid composition on the outer surface of the body facing material.

17 Claims, 2 Drawing Sheets

U.S. PATENT DOCUMENTS

| | | | |
|---|---|---|---|
| 5,192,606 A | | 3/1993 | Proxmire et al. |
| 5,288,546 A | | 2/1994 | Roessler et al. |
| 5,304,162 A | | 4/1994 | Kuen |
| 5,318,555 A | | 6/1994 | Siebers et al. |
| 5,364,382 A | | 11/1994 | Latimer et al. |
| 5,374,262 A | | 12/1994 | Keuhn, Jr. et al. |
| 5,386,595 A | | 2/1995 | Kuen et al. |
| 5,399,219 A | | 3/1995 | Roessler et al. |
| 5,403,302 A | | 4/1995 | Roessler et al. |
| 5,405,342 A | | 4/1995 | Roessler et al. |
| 5,413,570 A | | 5/1995 | Enloe |
| 5,415,644 A | | 5/1995 | Enloe |
| 5,423,789 A | | 6/1995 | Kuen |
| 5,429,629 A | | 7/1995 | Latimer et al. |
| 5,486,166 A | | 1/1996 | Bishop et al. |
| 5,490,846 A | | 2/1996 | Ellis et al. |
| 5,508,034 A | | 4/1996 | Bernstein |
| 5,509,915 A | | 4/1996 | Hanson et al. |
| 5,599,338 A | | 2/1997 | Enloe |
| 5,607,980 A | | 3/1997 | McAtee et al. |
| 5,643,588 A | * | 7/1997 | Roe et al. |
| 5,643,899 A | * | 7/1997 | Elias et al. |
| 5,648,083 A | | 7/1997 | Blieszner et al. |
| 5,651,862 A | | 7/1997 | Anderson et al. |
| 5,653,970 A | | 8/1997 | Vermeer |
| 5,656,278 A | | 8/1997 | Enjolras |
| 5,674,511 A | | 10/1997 | Kacher et al. |
| 5,738,859 A | | 4/1998 | Posner |
| 5,744,145 A | | 4/1998 | Bertoli et al. |
| 5,759,558 A | | 6/1998 | Epstein et al. |
| 5,800,818 A | | 9/1998 | Prugnaud et al. |
| 5,849,315 A | | 12/1998 | Rerek et al. |
| 5,863,663 A | | 1/1999 | Mackey et al. |
| 5,869,070 A | | 2/1999 | Dixon et al. |
| 5,968,025 A | | 10/1999 | Roe et al. |
| 6,086,858 A | | 7/2000 | McEleney et al. |
| 6,118,041 A | | 9/2000 | Roe et al. |
| 6,153,208 A | * | 11/2000 | Mcatee et al. |
| 6,287,286 B1 | | 9/2001 | Akin et al. |
| 6,287,581 B1 | | 9/2001 | Krzysik et al. |

FOREIGN PATENT DOCUMENTS

| | | |
|---|---|---|
| WO | WO 97/31620 A2 | 9/1997 |
| WO | WO 99/12519 A1 | 3/1999 |
| WO | WO 99/13861 A1 | 3/1999 |
| WO | WO 99/37744 A2 | 7/1999 |
| WO | WO 99/45973 A1 | 9/1999 |
| WO | WO 99/45974 A1 | 9/1999 |
| WO | WO 99/45976 A1 | 9/1999 |
| WO | WO 00/64407 A1 | 11/2000 |
| WO | WO 00/64408 A1 | 11/2000 |
| WO | WO 00/64409 A1 | 11/2000 |
| WO | WO 00/64501 A1 | 11/2000 |

OTHER PUBLICATIONS

American Society for Testing Materials (ASTM) Designation: D 1321–92, "Standard Test Method for Needle Penetration of Petroleum Waxes," pp. 483–485, published Dec. 1992.

American Society for Testing Materials (ASTM) Designation: E 96–92, "Standard Test Methods for Water Vapor Transmission of Materials," pp. 702–709, published Mar. 1992.

Derwent World Patent Database abstract of DE 4136540: Description of D. Pegaz, "Disposable Diaper".

Feingold, Kenneth R., MD, "Permeability Barrier Homeostasis: Its Biochemical Basis and Regulation," *Cosmetics & Toiletries*, vol. 112, Jul. 1997, pp. 49, 50, 53–59.

Fluhr, J.W. et al., "Glycerol Accelerates Recovery of Barrier Function In Vivo," *Acta Derm Venereol*, 1999; 79: pp. 418–421.

Ghadially, Ruby, MD, et al., "Effects of petrolatum on stratum corneum structure and function," *Journal of the American Academy of Dermatology*, vol. 26, No. 3, Mar. 1992, pp. 387–396.

Yang, L. et al., "Topical Stratum Corneum Lipids Accelerate Barrier Repair After Tape Stripping, Solvent Treatment And Some But Not All Types Of Detergent Treatment," *British Journal of Dermatology*, vol. 133, No. 5, Nov. 1995, pp. 679–685.

* cited by examiner

ABSORBENT ARTICLES PROVIDING SKIN HEALTH BENEFITS

This application is a continuation of application Ser. No. 09/379,928 entitled ABSORBENT ARTICLES PROVIDING SKIN HEALTH BENEFITS and filed in the U.S. Patent and Trademark Office on Aug. 24, 1999 now U.S. Pat. No. 6,287,581. The entirety of application Ser. No. 09/379,928 is hereby incorporated by reference.

FIELD OF THE INVENTION

The present invention relates to the inclusion of a lipid-enriched hydrophobic lotion on the body facing material of disposable absorbent articles, such as diapers, training pants, adult incontinence products, underpants, and feminine care products and the like. More particularly, the present invention relates to improving skin health via enhancement of skin barrier function by the delivery of lipid and non-lipid materials from the body facing material of disposable absorbent articles to the skin.

BACKGROUND OF THE INVENTION

The stratum corneum is the outer-most layer of the skin and is responsible for regulating skin water levels and functioning as a barrier against chemicals and other stressors found in the environment. The complex arrangement of lipids in the intercellular space of the stratum corneum is responsible for the establishment of normal barrier function. Multi-layered structures of cholesterol, ceramides, and fatty acids, as well as some other minor lipids, provides the major barrier to the transport of hydrophillic substances into the or through the skin. The link between the barrier function and skin health is apparent from the skin inflammation caused by lipid extraction from the skin.

Skin barrier can be damaged due to a number of mechanisms. Physical abrasion, for example caused by the repeated rubbing of abrasive materials, such as absorbent tissues or wipes, on the skin, strips away layers of the skin and thus damages skin barrier. Biological fluids, such as urine, feces and vaginal secretions, may contain a variety of components that can damage skin barrier. Examples of these components include proteases, lipases and bile acids. Once the skin barrier is compromised, these components, in addition to other constituents of biological fluids, can initiate or exacerbate skin inflammation.

Diaper dermatitis, for example, is a genre of skin conditions that, in large part, originate from impaired barrier function. Impairment of the skin barrier can result from a variety of factors, including; increased skin hydration due to the occlusion of the skin caused by diapers, enzymatic skin damage due to fecal and urinary enzymes, and physical damage caused by repeated cleaning of the skin with cloths or wet wipes.

Excessive hydration also has a negative impact on skin barrier. The hydration level of diapered skin, for example, may reach between five to ten times that of undiapered skin. Frequent contact of diapered skin with urine may also contribute to increased skin hydration. Increased skin hydration disrupts skin lipid organization in the stratum corneum. This disruption may increase the skin permeability of irritants from feces and urine, thus increasing the risk of skin inflammation.

Diapered skin is normally cleansed several times a day with wipes utilizing solutions containing surfactants. The surfactants can extract lipids from the stratum corneum or disorganize the lipid structure within the stratum corneum, thereby decreasing the barrier function. The wipe material can cause physical damage to the skin and thus lead to decreased barrier function.

Disposable absorbent articles such as diapers, training pants, adult incontinence products, absorbent under pants, and feminine care products have been used to absorb body fluids and leave the skin dry. Disposable absorbent articles of this type generally comprise a liquid impermeable back sheet member, an absorbent core or assembly, and a liquid permeable body facing material. It is the body facing material that comes into contact with the wearer's skin. While the body facing material is made of a soft compliant material, it can abrade the skin during use and may not leave the skin completely dry and free of the bodily fluids, such as solid or semi-solid waste, the absorbent article is trying to absorb. During frequent insults of bodily fluids and frequent use of disposable absorbent articles, the skin can become so abraded as to appear red and be sore to the touch.

Typically, barrier creams, lotions or ointments are used to provide an artificial hydrophobic barrier on the skin and treat skin conditions such as diaper rash. The application of these chemistries to the skin is often messy and inconvenient. They are typically used only when signs of diaper rash are apparent.

Diaper liners may be treated with emollients, such as petrolatum, that can be transferred to the skin through normal diapering practices. Once transferred to the skin, diaper liner formulations may provide an artificial barrier against feces and urine. These formulations may require high concentrations of petrolatum to ensure sufficient transfer to the skin for a health benefit. High concentrations of petrolatum can be messy, greasy to the touch, and may impair the fluid handling properties of an absorbent article, such as a diaper. The slow penetration of petrolatum into the skin can lead to smearing of the agent over the skin and onto clothes and other materials.

Thus, what is needed in the art is:

Topical chemistry delivered from a bodyside material of an absorbent article that protects, maintains, and/or recovers skin barrier against irritants in biological fluids.

Topical chemistry delivered from a bodyside material of an absorbent article that absorbs into the skin, is non-greasy and cosmetically acceptable to the consumer.

Topical chemistry delivered from a bodyside material of absorbent article that does not impair the waste containment functions of the diaper.

SUMMARY OF THE INVENTION

It has been discovered that superior skin barrier enhancing disposable absorbent articles can be made using a skin barrier enhancing, oil based-hydrophobic composition comprising from about 0.1 to about 95 weight percent natural fats or oils, from about 0.1 to about 10 weight percent—sterols and sterol derivatives, from about 0.5 to about 20 weight percent of humectant, from about 1 to about 20 weight percent of water-in-oil emulsifying surfactant/surfactant combination having an HLB range from about 3 to about 6, from about 5 to about 95 weight percent emollient, from about 5 to about 95 weight percent wax, and from about 1 to about 25 weight percent viscosity enhancer. The composition may have a melting point from about 30° C. to about 100° C. and a process viscosity of greater than about 50 centipoise. Also, the composition may have a penetration hardness of from about 5 millimeters to 360 millimeters.

Hence, in one aspect, the present invention is a skin barrier enhancing disposable absorbent article that can be made applying, on the outer surface of the body facing material, a melted lipid-enriched hydrophobic composition comprising an emollient, a wax, a viscosity enhancer, a humectant, a water-in-oil emulsifying surfactant having an HLB range from about 3 to about 6, a sterol and sterol derivative, and a natural fat or oil, and thereafter resolidifying the composition to form a distribution on the outer surface of the body facing material. Because the composition is a solid at room temperature and rapidly solidifies after application, it has less tendency to penetrate and migrate into the body facing material. Compared to body facing materials treated with liquid formulations, this leaves a greater percentage of the added solid lotion composition on the surface of the body facing material where it can contact and transfer to the user's skin to provide enhanced skin health benefits. Furthermore, a lower add-on amount can be used to deliver the same benefit at a lower cost because of the efficient placement of the composition substantially at the surface of the body facing material of the absorbent articles.

In another aspect, the present invention is a body facing material wherein the outer surface of the material has solidified deposits of an oil based-hydrophobic composition comprising from about 0.1 to about 95 weight percent natural fats or oils, from about 0.1 to about 10 weight percent sterols and sterol derivatives, from about 0.5 to about 20 weight percent of humectant, from about 1 to about 20 weight percent of water-in-oil emulsifying surfactant/ surfactant combination having an HLB range from about 3 to about 6, from about 5 to about 95 weight percent emollient, from about 5 to about 95 weight percent wax, and from about 1 to about 25 weight percent viscosity enhancer. The composition may have a melting/freezing point of from about 30° C. to about 100° C. and a process viscosity of greater than about 50 centipoise. Also, the composition may have a penetration hardness from about 5 millimeters of penetration to 360 millimeters of penetration.

In another aspect, the present invention resides in a method of treating a body facing material with a composition by comprising: (a) a natural fat or oil, a sterols and sterol combinations, humectant, a water-in-oil emulsifying surfactant(s) having an HBL range from about 3 to about 6, an emollient, a wax, and a viscosity enhancer, to a temperature above the melting point of the composition, causing the composition to melt; (b) uniformly applying the melted composition to the outer surface of the body facing material; and (c) resolidifying the melted composition. The composition may have a melting point ranging from about 30° C. to about 100° C.

DETAILED DESCRIPTION OF THE INVENTION

Figure 1:
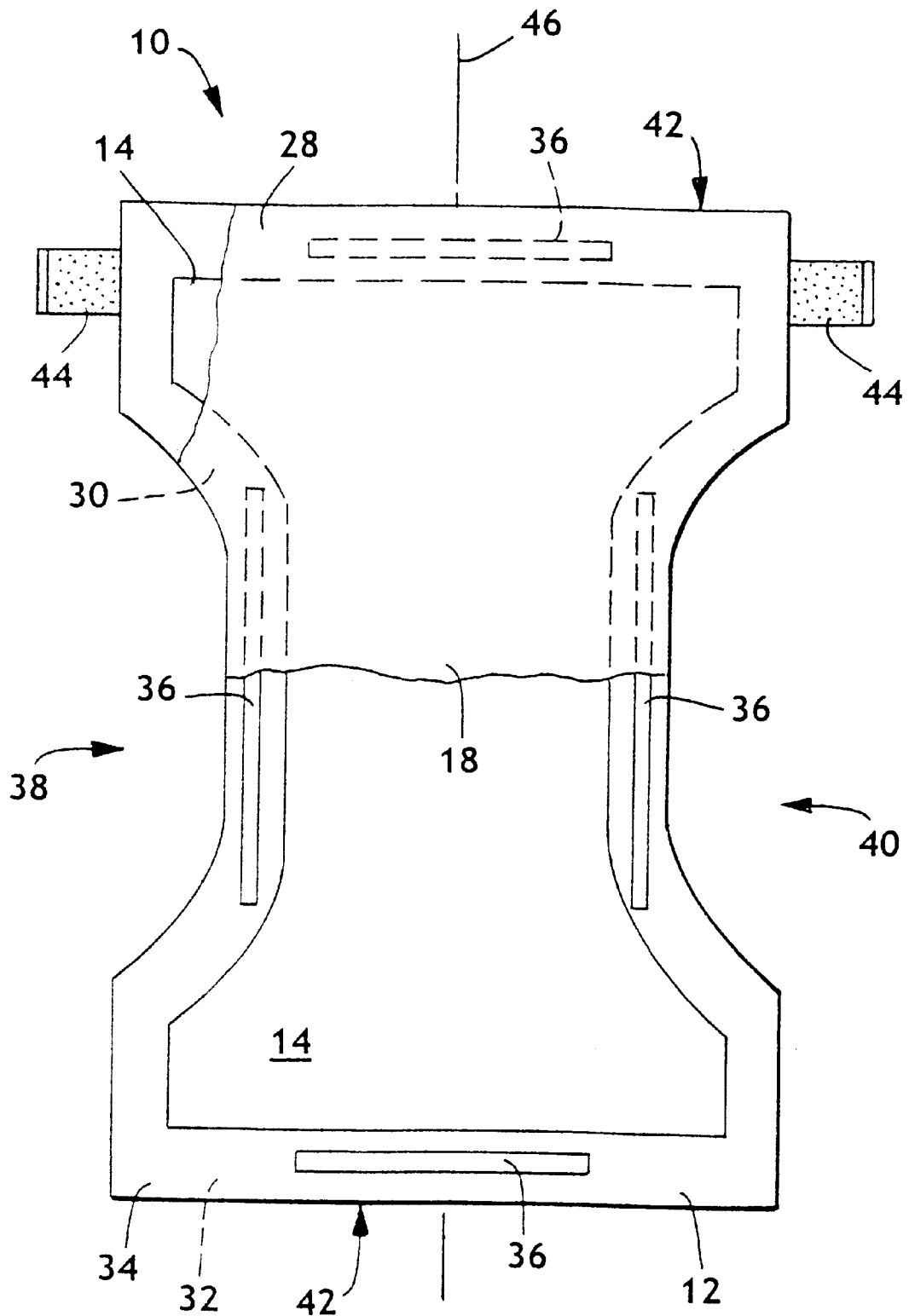
FIG. 1 representatively shows a partially cutaway, top plan view of an absorbent article according to one embodiment of the present invention.

One embodiment of the present invention is a body facing material containing a composition that enhances skin barrier. The composition may comprise from about 0.1 to about 95 weight percent of natural fats or oils, from about 0.1 to about 10 weight percent of sterols or sterol derivatives, from about 1 to about 20 weight percent of water-in-oil emulsifying surfactant having an HLB range from about 3 to about 6, from about 0.5 to about 20 weight percent of humectant, from about 5 to about 95 weight percent of emollient, from about 5 to about 95 weight percent of wax, and from about 1 to about 25 weight percent of viscosity enhancer.

The composition may have a melting point from about 30° C. to about 100° C. The composition may have a process viscosity of greater than about 50 centipoise. The composition may have a penetration hardness of from about 5 millimeters to about 360 millimeters. The add-on amount of the composition may be from about 0.1 grams per meter squared (g/m$^2$) to about 30 g/m$^2$ of the material, and more preferably from about 0.5 g/m$^2$ to about 25 g/m$^2$.

The natural fat or oil used in the composition may include sunflower oil, borage, or avocado oil. The sterol or sterol derivative used in the composition may include soy sterol, cholesterol, or lanasterol. The humectant used in the composition may include glycerin, sorbitol, or hydrogenated starch hydrolysate. The emulsifying surfactant used in the composition may include sorbitan oleate, glyceryl stearate, or sorbitan stearate. The emollient used in the composition may include petrolatum, mineral oil, or cosmetic esters. The wax used in the composition may include ozokerite, cerasin, or microcrystalline wax. The viscosity enhancer used in the composition may include ethylene/vinyl acetate copolymer or polyethylene.

Another embodiment of the present invention is a method of treating a body facing material with a composition that enhances skin barrier by: (a) heating a composition comprising a natural fat or oil, a sterol or sterol derivative, a humectant, a water-in-oil emulsifying surfactant having an HLB range from about 3 to about 6, an emollient, a wax, and a viscosity enhancer, to a temperature above the melting point of the composition, causing the composition to melt; (b) applying the melted composition to the outer surface of a body facing material web in spaced-apart deposits; and (c) resolidifying the deposits of the melted composition. The melted composition may be applied by spraying, slot coating, or printing.

Another embodiment of the present invention is a skin barrier enhancing composition comprising from about 0.1 to about 95 weight percent of natural fats or oils, from about 0.1 to about 10 weight percent of sterols and sterol derivatives, from about 1 to about 20 weight percent of water-in-oil emulsifying surfactant having an HLB range from about 3 to about 6, from about 0.5 to about 20 weight percent of humectant, from about 5 to about 95 weight percent of emollient, from about 5 to about 95 weight percent of wax, and from about 1 to about 25 weight percent of viscosity enhancer.

The natural fats or oils of the composition may be selected from the group consisting of: avocado oil, apricot oil, babassu oil, borage oil, camellia oil, canola oil, castor oil, chamomile, coconut oil, corn oil, cottonseed oil, evening primrose oil, hemp seed, hydrogenated cottonseed oil, hydrogenated palm kernel oil, maleated soybean oil, meadowfoam oil, palm kernel oil, phospholipids, rapeseed oil, palmitic acid, stearic acid, linoleic acid, rose hip oil, safflower, sunflower oil, soybean oil, sweet almond, PRO-LIPID 141, or derivatives of natural fats or oils (such as stearyl alcohol, lauryl alcohol, myristyl alcohol, and benenyl alcohol, and the like), and mixtures thereof. (PROLIPID is commercially available from International Specialty Products located in Wayne, N.J. PROLIPID is generally described in U.S. Pat. No. 5,849,315 to Rerek et al. which issued Dec. 15, 1998; the entire disclosure of which is herein incorporated by reference to the extent it is consistent herewith.)

The sterol and sterol derivative of the composition may be selected from the group consisting of: cholesterol, sitosterol, stigmasterol, and ergosterol, lanasterol, soy sterol, avocado sterols, CRODAROM AVOCADIN, sterol esters, and mixtures thereof. The emulsifying surfactant of the composition may be selected from the group consisting of: sorbitan monooleate, sorbitan sequioleate, sorbitan trioleate, sorbitan stearate, sorbitan tristearate, and mixtures thereof. (Crodarom Avocadin is commercially available from Croda, Inc. located in Parsippany, N.J.)

The humectant of the composition may be selected from the group consisting of: glycerin, hydrogenated starch hydrolysate, propylene glycol, sodium PCA, sodium lactate, sorbitol, and mixtures thereof. The emollient of the composition may be selected from the group consisting of: mineral oils, mineral jellys, petrolatum, cosmetic esters, and mixtures thereof. The wax of the composition may be selected from the group consisting of: carnuba, cerasin, cetyl esters, microcrystalline wax, montan wax, ozokerite, synthetic wax, and mixtures thereof. The viscosity enhancer of the composition may be selected from the group consisting of: polyolefin resins, polyolefin polymers, ethylene/vinyl acetate copolymers, polyethylene and mixtures thereof.

The amount of the natural fats or oils used in the composition may be from about 0.1 to about 95 weight percent. The amount of the sterols and sterol derivatives used in the composition may be from about 0.1 to about 10 percent. The amount of the emulsifying surfactant used in the composition may be from about 1 to about 20 weight percent. The amount of the humectant used in the composition may be from about 0.5 to about 20 weight percent. The amount of the emollient used in the composition may be from about 5 to about 95 weight percent. The amount of the wax used in the composition may be from about 5 to about 95 weight percent. The amount of the viscosity enhancer used in the composition may be from about 1 to about 25 weight percent.

One embodiment of the composition comprises about 10 weight percent sunflower oil, about 0.8 weight percent soy sterol, about 1 weight percent sorbitan oleate, about 5 weight percent glycerin, about 31.2 weight percent petrolatum, about 45 weight percent blend of microcrystalline cetyl esters and ozokerite, and about 7 weight percent viscosity ethylene/vinyl acetate copolymer. The blend of microcrystalline wax, cetyl esters, and ozokerite is from about 10 to about 20 weight percent microcrystalline wax, about 10 to about 20 weight percent cetyl esters, and about 60 to about 80 weight percent ozokerite.

Another embodiment of the composition comprises about 10 weight percent borage oil, about 0.8 weight percent soy sterol, about 1 weight percent sorbitan oleate, about 5 weight percent glycerin, about 26.2 weight percent petrolatum, about 50 weight percent wax, and about 7 weight percent viscosity ethylene/vinyl acetate copolymer.

Another embodiment of the composition comprises about 10 weight percent avocado oil, about 0.8 weight percent soy sterol, about 1 weight percent sorbitan oleate, about 5 weight percent glycerin, about 31.2 weight percent petrolatum, about 45 weight percent of a blend of ozokerite, cetyl esters, microcrystlline wax, and about 7 weight percent viscosity ethylene/vinyl acetate copolymer. The blend of microcrystalline wax, cetyl esters, and ozokerite is about 10 to about 20 weight percent microcrystalline wax, about 10 to about 20 weight percent cetyl esters, and about 60 to about 80 weight percent ozokerite.

Another embodiment of the composition comprises about 2 weight percent PROLIPID 141 (International Specialty Products, Wayne, N.J.), about 10 weight percent sunflower oil, about 1 weight percent soy sterol, about 1 weight percent sorbitan oleate, about 5 weight percent glycerin, about 34 weight percent petrolatum, about 32 weight percent cerasin, and about 15 weight percent viscosity polyethylene.

Another embodiment of the composition comprises about 2 weight percent PROLIPID 141 (International Specialty Products, Wayne, N.J.), about 30 weight percent sunflower oil, about 3 weight percent soy sterol, about 5 weight percent sorbitan oleate, about 5 weight percent sorbitol, about 5 weight percent petrolatum, about 40 weight percent ozokerite, and about 10 weight percent polyethylene.

Another embodiment of the composition comprises about 5 weight percent lanolin, about 25 weight percent sunflower oil, about 3 weight percent cholesterol, about 5 weight percent sorbitan stearate, about 5 weight percent hydrogenated starch hydrolysate, about 2 weight percent petrolatum, about 40 weight percent blend of ozokerite and microcrystalline wax, and about 15 weight percent polyethylene. The blend of microcrystalline wax and ozokerite is about 40 weight percent microcrystalline wax and about 60 weight percent ozokerite.

Another embodiment of the composition comprises about 27 weight percent avocado oil, about 3 weight percent avocadin or avocado sterols, about 2 weight percent glyceryl stearate, about 15 weight percent glycerin, about 3 weight percent petrolatum, about 40 weight percent ozokerite, and about 10 weight percent polyethylene.

Another embodiment of the composition comprises about 15 weight percent avocado oil, about 5 weight percent sterol esters, about 10 weight percent glyceryl stearate, about 8 weight percent glycerin, about 2 weight percent petrolatum, about 55 weight percent of a blend of ozokerite and cetyl esters, and about 5 weight percent polyethylene. The blend of cetyl esters and ozokerite is about 10 weight percent cetyl esters, and about 90 weight percent ozokerite.

Another embodiment of the composition comprises about 45 weight percent borage oil, about 10 weight percent avocadin or avocado sterols, about 5 weight percent glyceryl stearate, about 1 weight percent glycerin, about 1 weight percent petrolatum, about 36 weight percent cerasin, and about 2 weight percent polyethylene.

Another embodiment of the composition comprises about 25 weight percent sunflower oil, about 3 weight percent lanasterol, about 2 weight percent glyceryl stearate, about 5 weight percent glycerin, about 15 weight percent petrolatum, about 45 weight percent of a blend of ozokerite and microcrystalline wax, and about 5 weight percent polyethylene. The blend of microcrystalline wax and ozokerite is about 10 weight percent microcrystalline wax and about 90 weight percent ozokerite.

Another embodiment of the composition comprises about 35 weight percent avocado oil, about 3 weight percent sitosterol, about 5 weight percent sorbitan trioleate, about 5 weight percent glycerin, about 1 weight percent petrolatum, about 41 weight percent ozokerite, and about 10 weight percent polyethylene.

Another embodiment of the present invention is a method for enhancing/restoring/maintaining the skin barrier function of a user of absorbent articles. The method comprises the steps of:

a) contacting the skin of the user with a body facing material wherein the body facing material comprises a skin barrier enhancing/restoring/maintaining composition that provides a skin barrier enhancing/restoring/maintaining benefit upon transfer of the composition from the body facing material to the user's skin;

b) transferring at least a portion of the composition from the body facing material to the user's skin during use of the absorbent article; and, c) repeating steps a) and b) with one or more additional body facing material with sufficient frequency to enhance/restore/maintain said skin barrier in an area of skin contacted by the body facing material, relative to skin contacted by an equivalent body facing material that does not comprise the skin barrier enhancing/restoring/maintaining composition.

The skin barrier enhancing/restoring/maintaining composition of the method comprises from about 0.1 to about 95 weight percent of natural fats or oils, from about 0.1 to about 10 weight percent of sterols and sterol derivatives, from about 1 to about 20 weight percent of water-in-oil emulsifying surfactant having an HLB range from about 3 to about 6, from about 0.5 to about 20 weight percent of humectant, from about 5 to about 95 weight percent of emollient, from about 5 to about 95 weight percent of wax, and from about 1 to about 25 weight percent of viscosity enhancer.

The composition may have a melting point from about 30° C. to about 100° C. The resolidified composition may have a process viscosity greater than about 50 centipoise. The resolidified composition may have a penetration hardness of from about 5 to about 360 millimeters. The method may further comprise using a body facing material having a skin-barrier enhancing/restoring/maintaining composition by the user on each use occasion. The method may further comprise using a body facing material which does not comprise a skin-barrier enhancing/restoring/maintaining composition by the user intermittently. The method may further comprise using the body facing material comprising a skin-barrier enhancing/restoring/maintaining composition by a user whose skin is compromised and with sufficient frequency to improve skin-barrier function.

The amount of a natural fat or oil or a mixture of natural fats or oils in the oil based-hydrophobic composition can be from about 0.1 to about 95 weight percent, more specifically from about 5 to about 75 weight percent, more specifically from about 10 to about 50 weight percent. As used herein, the phrase natural fats or oils is understood to include fats, oils, essential oils, fatty acids, fatty alcohols, phospholipids, and mixtures thereof. As used herein, suitable natural fats or oils include, but are not limited to, the following materials classified according to CTFA designations:

Fats and Oils:

Apricot Kernel Oil, Avocado Oil, Babassu Oil, Borage Seed Oil, Butter, $C_{12}$–$C_{18}$ Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, $C_{10}$–$C_{18}$ Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated $C_{12}$–$C_{18}$ Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lanolin and Lanolin Derivatives, Lard, Lauric/Palmitic/Oleic Triglyceride, Lesquerella Oil, Linseed Oil, Macadamia Nut Oil, Maleated Soybean Oil, Meadowfoam Seed Oil, Menhaden Oil, Mink Oil, Moringa Oil, Mortierella Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, and the like, as well as mixtures thereof.

Fatty Acids:

Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Fatty Alcohols:

Behenyl Alcohol, $C_9$–$C_{11}$ Alcohols, $C_{12}$–$C_{13}$ Alcohols, $C_{12}$–$C_{15}$ Alcohols, $C_{12}$–$C_{16}$ Alcohols, $C_{14}$–$C_{15}$ Alcohols, Caprylic Alcohol, Cetearyl Alcohol, Cetyl Alcohol, Coconut Alcohol, Decyl Alcohol, Hydrogenated Tallow Alcohol, Lauryl Alcohol, Myristyl Alcohol, Oleyl Alcohol, Palm Alcohol, Palm Kernel Alcohol, Stearyl Alcohol, Tallow Alcohol, Tridecyl Alcohol, and the like, as well as mixtures thereof.

Essential Oils:

Anise Oil, Balm Mint Oil, Basil Oil, Bee Balm Oil, Bergamot Oil, Birch Oil, Bitter Almond Oil, Bitter Orange Oil, Calendula Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, Sambucus Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

The preferred natural fats or oils include, but not limited to: Avocado Oil, Apricot Oil, Babassu Oil, Borage Oil, Camellia oil, Canola oil, Castor Oil, Coconut oil, Corn Oil, Cottonseed Oil, Evening Primrose Oil, Hydrogenated Cottonseed Oil, Hydrogenated Palm Kernal Oil, Maleated Soybean Oil, Meadowfoam Oil, Palm Kernel Oil, Phospholipids, Rapeseed Oil, Palmitic Acid, Stearic Acid, Linoleic Acid, Stearyl Alcohol, Lauryl Alcohol, Myristyl Alcohol, Benenyl Alcohol, Rose Hip Oil, Sunflower Oil, Soybean Oil, PROLIPID 141 (proprietary blend of Glyceryl Stearate, Fatty Acids, Fatty Alcohols, and Phospholipids from International Specialty Products, Wayne, N.J.) and the like, as well as mixtures thereof.

The amount of sterols or sterol derivative or mixture thereof in the oil based-hydrophobic composition can be from about 0.1 to about 10 weight percent, more specifically from about 0.5 to about 5 weight percent, and still more specifically from about 0.8 to about 1 weight percent. As used herein, suitable sterols and sterol derivatives include, but are not limited to, the following materials: β-sterols having a tail on the 17 position and having no polar groups for example cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyidecanoate, dihydrolanosterol, dihydrolanosteryl octyldecanoate, ergocalciferol, tall oil sterol, soy sterol acetate, lanasterol, soy sterol, avocado sterols, avocadin, sterol esters, and the like, as well as mixtures thereof.

The amount of water-in-oil emulsifying surfactant surfactant combination with an HLB range from about 3 to about 6 in the oil based-hydrophobic composition can be from about 1 to about 20 weight percent, more specifically from about 2 to about 10 weight percent, and still more specifically from about 3 to about 8 weight percent. Emulsifying surfactants are employed typically in cosmetic preparations to form emulsions of various components. The immiscible phase, such as water and water soluble/dispersible materials, is dispersed as droplets in the continuous phase, such as an oil.

The preferred surfactants and surfactant combinations with an HLB of from about 3 to about 6, include, but are not limited to: Sorbitan monooleate, sorbitan sequioleate, sorbitan trioleate, glyceryl stearate, sorbitan stearate, sorbitan tristearate, and the like, as well as mixtures thereof.

The amount of humectant in the oil based-hydrophobic composition can be from about 0.5 to about 20 weight percent, more specifically from about 1 to about 15 weight percent, and still more specifically from about 3 to about 10 weight percent. Humectants are typically cosmetic ingredients used to increase the water content of the top layers of the skin. This group of materials includes primarily hydroscopic ingredients. As used herein, suitable humectants include, but are not limited to, the following materials Acetamide MEA, Aloe Vera Gel, Arginine PCA, Chitosan PCA, Copper PCA, Corn Glycerides, Dimethyl Imidazolidinone, Fructose, Glucamine, Glucose, Glucose Glutamate, Glucuronic Acid, Glutamic Acid, Glycereth-7, Glycereth-12, Glycereth-20, Glycereth-26, Glycerin, Honey, Hydrogenated Honey, Hydrogenated Starch Hydrolysate, Hydrolyzed Corn Starch, Lactamide MEA, Lactic Acid, Lactose Lysine PCA, Mannitol, Methyl Gluceth-10, Methyl Gluceth-20, PCA, PEG-2 Lactamide, PEG-10 Propylene Glycol, Polyamino Sugar Condensate, Potassium PCA, Propylene Glycol, Propylene Glycol Citrate, Saccharide Hydrolysate, Saccharide Isomerate, Sodium Aspartate, Sodium Lactate, Sodium PCA, Sorbitol, TEA-Lactate, TEA-PCA, Urea, Xylitol, and the like, as well as mixtures thereof.

The preferred humectants include, but are not limited to: Glycerin, Hydrogenated Starch Hydrolysate, Propylene glycol, Sodium PCA, Sodium Lactate, Sorbitol and the like, as well as mixtures thereof.

The amount of emollient in the oil based-hydrophobic composition can be from about 5 to about 95 weight percent, more specifically from about 15 to about 80 weight percent, and still more specifically from about 20 to about 65 weight percent. As used herein, suitable emollients include, but are not limited to, the following materials: Mineral Oil, Mineral Jelly, Petrolatum, cosmetic esters, fatty esters, glyceryl esters, alkoxylated carboxylic acids, alkoxylated alcohols, fatty alcohols, lanolin and lanolin derivatives, petrolatum base oils, silicones, fats, hydrogenated vegetable oils, polyhydroxy esters, and the like, as well as mixtures thereof.

The amount of wax in the oil based-hydrophobic composition can be from about 5 to about 95 weight percent, more specifically from about 10 to about 75 weight percent, and still more specifically from about 20 to about 60 weight percent. As used herein, suitable waxes include, but are not limited to, the following materials: natural and synthetic waxes, such as bayberry wax, beeswax, $C_{30}$ alkyl dimethicone, candelilla wax, carnuaba, ceresin, cetyl esters, hydrogenated cottonseed oil, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, motan acid wax, motan wax, ouricury wax, ozokerite, paraffin, PEG-6 beeswax, PEG-8 beeswax, rice bran wax, shellac wax, spent grain wax, steryl dimethicone synthetic beeswax, synthetic candelilla wax, synthetic carnuba wax, synthetic japan wax. Synthetic jojoba wax, synthetic wax, and the like, as well as mixtures thereof.

The preferred waxes include but are not limited to; carnuba, cerasin, cetyl esters, microcrystalline wax, montan wax, ozokerite, synthetic wax, and the like, as well as mixtures thereof.

The amount of viscosity enhancer in the oil based-hydrophobic composition can be from about 1 to about 25 weight percent, more specifically from about 5 to about 20 weight percent, and still more specifically from about 10 to about 15 weight percent. As used herein, suitable viscosity enhancers include, but are not limited to, the following materials: the group consisting of polyolefin resins, polyolefin polymers, ethylene/vinyl acetate copolymers, polyethylene, and the like, as well as mixtures thereof.

As used herein, the term 'body facing material'0 includes, but is not limited to, materials such as: body side liner; elastic material; tissue; intake and distribution material, absorbent material, including, but not limited to coform, woven and nonwoven materials, back sheet liner material, or any other material known in the art that are or can be used in the construction of personal care absorbent articles, such as diapers, training pants, absorbent underpants, adult incontinence product, feminine hygiene products. The term 'body facing material' is understood to include materials that are both typically and less frequently in contact with the wearer's skin. The body facing material of the present invention can be a single layer or multi-layers.

The composition of the present invention can be applied to a specific portion or component of the absorbent article or to the entire surface of the absorbent article that comes into contact with the wearer's skin during use of the absorbent article. In addition, the composition can be applied in varying concentration or deposition amounts on the skin contacting surface of the absorbent article or portion thereof. The compositions are applied such that the compositions will be delivered via contact with the user's skin during the use of the absorbent article. The compositions of the present invention can be applied after the body facing material has been incorporated into the absorbent article or prior to incorporating the body facing material into the absorbent article. The phrase 'effective amount of the composition' is understood to mean an amount of the composition of the present invention which, when applied to the body facing material, will be effective in providing skin barrier enhancing benefits.

Some additional examples of materials that may serve as body facing material in the present invention are discussed in the following patent applications: "Absorbent Article Having Improved Breathability", U.S. Ser. No. 09/139,820, Attorney docket number 13,732, filed on Aug. 25, 1998 with Michael J. Faulks and Pamela J. Mayberry as inventors; "Absorbent Article Having a High Air Exchange Rate", U.S. Ser. No. 09/139,824, Attorney docket number 13,827, filed on Aug. 25, 1998 with Michael J. Faulks, Pamela J. Mayberry, Sue C. Paul, Audra S. Wright, and Frank J. Akin as inventors; and, "Absorbent Article Having a Reduced Growth of Candida Albican S", U.S. Ser. No. 09/328,681, Attorney docket number 14,270, filed on Jun. 9, 1999 (claiming priority to a provisional application filed Aug. 25, 1998 with U.S. Ser. No. 60/097,810 PROV) with Michael J. Faulks, Pamela J. Mayberry, Sue C. Paul, and Audra S. Wright as inventors, the entire disclosures of which are herein incorporated by reference to the extent it is consistent herewith.

Resolidification of the melted oil based-hydrophobic composition can occur almost instantaneously, without the need for external cooling means such as chill rolls, if the composition is heated to a temperature only slightly above or at the melting point of the composition. However, external means such as chill rolls, either before or after the application of melt, can be used if desired to accelerate resolidification. Such instantaneous resolidification tends to impede penetration of the composition into the bodyside liner 18 or tissue material 20 and retain it on the outer surface 28 of the bodyside liner 18 or tissue material 20, which is advantageous. For example, the temperature of the melted composition can advantageously be above the melting point about 10° C. or less, more specifically about 5° C. or less and still more specifically about 2° C. or less. As the temperature of the melted composition approaches the melting point, the viscosity of the melted composition generally increases, which further enhances the tendency of the melted composition to be retained on the outer surface 28.

For purposes herein, "melting point" is the temperature at which the majority of the melting occurs, it being recognized that melting actually occurs over a range of temperatures. The melting point of the compositions of this invention can be from about 30° C. to about 100° C., more specifically from about 40° C. to about 80° C., and still more specifically from about 50° C. to about 60° C.

In addition, for purposes herein, "penetration hardness" is the needle penetration in millimeters according to ASTM D 1321, "Needle Penetration of Petroleum Waxes. Lower needle penetration hardness values correspond to harder materials. The penetration hardness of the compositions of this invention can be from about 5 to 360 millimeters, more specifically from about 5 to about 200 millimeters, more specifically from about 20 to about 150 millimeters, and still more specifically from about 40 to about 100 millimeters. (Formulations having a needle penetration hardness greater than 360 millimeters cannot be measured using ASTM method D 1321).

The hardness of the formulations or compositions of this invention is important for two reasons. First, the softer the formulation the more mobile the formulation will be, making the formulation more likely to migrate to the interior of the bodyside liner 18 or 20 as well as the absorbent core 14, which is not desirable. Secondly, softer formulations tend to be more greasy/oily to the touch, which is also less desirable. In general, formulations having a needle penetration hardness of from about 200 to 360 millimeters feel creamy to slightly greasy with less smoothness (depending on additives). Formulations that have needle penetration hardness values of from about 5 to about 200 millimeters feel silky to creamy and very smooth (depending on additives).

The melt point viscosity and/or the process temperature viscosity of the formulations or compositions of this invention is important for two reasons. First, the higher the melt point viscosity or the process temperature viscosity as it is applied to the outer surface 28 of the bodyside liner 18 or tissue material 20, the formulation is less likely to penetrate through to the inner surface 30 of the bodyside liner 18 or tissue material 20. The less the formulation is able to penetrate through the bodyside liner 18 or tissue material 20, the more formulation on the outer surface 28 of the bodyside liner 18 or tissue material 20 where the formulation can readily transfer to the surface of the wearer's skin.

Secondly, the higher the viscosity of the formulation at or above the melting point of the formulation, the less likely the formulation will migrate at typical or adverse storage conditions.

In order to better enhance the benefits to consumers, additional ingredients can be used. The classes of ingredients and their corresponding benefits include, without limitation: antifoaming agents (reduce the tendency of foaming during processing); antimicrobial actives; antifungal actives; antiseptic actives; antioxidants (product integrity to prevent oxidation of natural oils and other ingredients on the formulation or composition); astringents—cosmetic (induce a tightening or tingling sensation on skin); astringent—drug (a drug product which checks oozing, discharge, or bleeding when applied to skin or mucous membrane and works by coagulating protein); biological additives (enhance the performance or consumer appeal of the product including vitamins); colorants (impart color to the product); deodorants (reduce or eliminate unpleasant odor and protect against the formation of malodor on body surfaces); emollients (help to maintain the soft, smooth, and pliable appearance of the skin by their ability to remain on the skin surface or in the stratum corneum to act as lubricants, to reduce flaking, and to improve the skin's appearance); film formers (to hold active ingredients on the skin by producing a continuous film on skin upon drying); fragrances (consumer appeal); lubricants, such as silicones and organomodified silicones; natural moisturizing agents (NMF) and other skin moisturizing ingredients known in the art; skin conditioning agents; skin exfoliating agents (ingredients that increase the rate of skin cell turnover such as alpha hydroxy acids and beta hydroxyacids); skin protectants (a drug product which protects injured or exposed skin or mucous membrane surface from harmful or annoying stimuli); solvents (liquids employed to dissolve components found useful in the cosmetics or drugs); UV absorbers; and, surfactants (as cleansing agents solubilizing agents, suspending agents, and wetting agents).

The minimum level of the composition to be applied to the bodyside liner 18 or tissue material 20 is an amount effective for reducing abrasion or irritation of the skin of the wearer. The total bodyside liner 18 or tissue material 20 add-on of the composition can be from about 0.05 to about 100 mg/cm$^2$, desirably from about 1 to about 50 mg/cm$^2$ and more desirably from about 10 to about 40 mg/cm$^2$ based on the weight of the bodyside liner 18 or tissue material 20. The add-on amount will depend upon the desired effect of the composition on the product attributes and the specific composition.

A preferred method to uniformly apply the heated composition to the outer surface 28 of the web of the bodyside liner 18 or tissue material 20 is spraying or slot-coating. However, other methods, such as flexographic, roto-gravure printing, and spraying, such as WEKO, can be used.

As used herein, all recited ranges of amounts, temperatures, molecular weights and penetration hardnesses are intended to include all sub-ranges within the recited ranges, even though not specifically stated.

As used herein, the term "absorbent article" refers to articles or products that are used to absorb and contain bodily fluids. Disposable absorbent articles 10 include such products as diapers, training pants, adult incontinence articles, absorbent under pants, and feminine care products that have been used to absorb body fluids and leave the skin dry.

Figure 2:
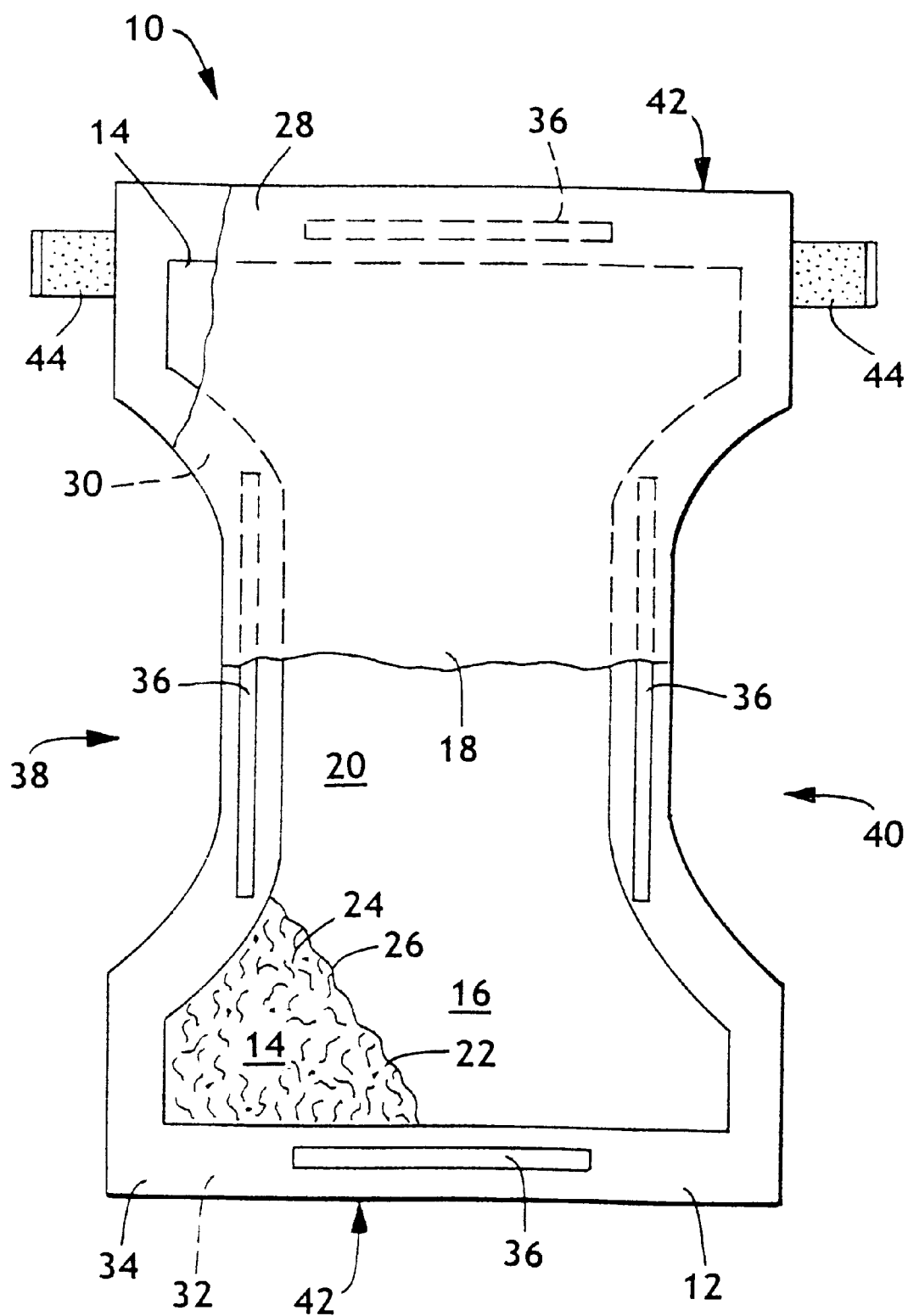
FIG. 2 representatively shows a partially cutaway, top plan view of an absorbent article according to another embodiment of the present invention.

Disposable absorbent articles 10 of this type generally comprise a liquid impermeable back sheet member 12, an absorbent core 14 or absorbent assembly 16, and a liquid permeable bodyside liner 18. (See FIGS. 1 and 2.) It is the bodyside liner 18 or the tissue material 20 that comes into contact with the wearer's skin. Typically, the back sheet member 12 is joined to the bodyside liner 18 with the absorbent core 14 disposed between the back sheet member 12 and the bodyside liner 18. A general description of these components, the back sheet member 12, the bodyside liner 18, and the absorbent core 14, will be discussed below.

In general, the absorbent core 14 absorbs and retains bodily fluids, such as urine, menses, and other body exudates. The absorbent core 14 is preferably compressible, conformable, and non-irritating to the wearer's skin. The absorbent core 14 may take a variety of sizes and shapes, such as rectangular, oval, hourglass, "T" shaped, asymmetric, dog bone, and the like. The absorbent core 14 may be comprised of a wide variety of liquid absorbent materials commonly used in absorbent articles 10. Absorbent cores 14 typically include a porous fibrous matrix 22 and high absorbency material 24.

The porous fibrous matrix 22 of absorbent core 14 is preferably an air laid batt of fluff and high absorbency material 24 which may be formed in many ways, for example according to the teaching of Mazurak and Fries as set forth in U.S. Pat. No. 4,381,782 the entire disclosure of which is incorporated herein by reference to the extent it is consistent herewith. The absorbent core 14 can comprise an air-formed mixture of high absorbency material 24 (SAP) and fibers 22, preferably of fluff pulp. The mixing of the fluff fibers 22 and the high absorbency material 24 can be homogeneous, graduated, or layered. Also, the fibers 22, other than fluff pulp such as chemically stiffened and thermo-mechanical pulps, can be used.

In addition, the absorbent core 14 can comprise absorbent material other than air formed fluff 22 and SAP 24. For example, coform materials as referenced in U.S. Pat. No. 4,818,464 to Lau and U.S. Pat. No. 4,100,324 to Anderson can be used to make the absorbent as long as they also contain high absorbency materials. In addition, wet formed composite materials comprising a combination of fibers and high absorbency materials as disclosed in U.S. Pat. No. 5,651,862 to Anderson et al. can also be used. Stabilized air-laid materials comprising a mixture of fibers, binder fibers, and high absorbency materials which are bound together by latex binding or through air bonding are also usable as absorbent materials. Additionally, any material known in the art that serves to absorb body exudates can be used to construct the absorbent core 14 as shown in the present invention.

The high absorbency materials 24 are typically hydrogel polymers that are desirably sufficiently cross-linked to render the materials substantially water-insoluble. Cross-linking may, for example, be by irradiation or by covalent, ionic, van der Waals or hydrogen bonding. Suitable materials are available from various commercial vendors, such as Dow Chemical Company (Drytech 2035 LD), Hoechst-Celanese Corporation and Allied-Colloid. Typically, the high-absorbency material 24 is capable of absorbing at least about 15 times its weight in water, and desirably is capable of absorbing more than about 25 times its weight in water.

The high-absorbency material 24 can be distributed or otherwise incorporated into the absorbent core 14 employing various techniques. For example, the high-absorbency material 24 can be substantially uniformly distributed among the fibers 22 comprising the absorbent core 14. The material 24 can also be non-uniformly distributed within the fibers 22 of the absorbent core 14 to form a generally continuous gradient with either an increasing or decreasing concentration of high-absorbency material 24, as determined by observing the concentration moving inward from the back sheet member 12. Alternatively, the high-absorbency material 24 can comprise a discrete layer separate from the fibers 22 of the absorbent core 14, or can comprise a discrete layer integral with the absorbent core 14.

The absorbent core 14 may also include a wrap layer 26 to help maintain the integrity of the fibrous absorbent core 14. (See FIG. 2.) This wrap layer 26 may comprise a cellulosic tissue or spunbond, meltblown or bonded-carded web material composed of synthetic polymer filaments, such as polypropylene, polyethylene, polyesters or the like or natural polymer filaments such as rayon or cotton. The wrap layer 26 may be made of the same materials as those used in the bodyside liner 18 or be made of materials differing from those used in the bodyside liner 18. In some cases, the bodyside liner 18 may be absent, and the wrap layer 26, also referred to as tissue material 20, will serve as the bodyside layer 18 of the absorbent article 10, coming in contact with the wearer's skin.

The absorbent core 14 can include additional components to assist in the acquisition, distribution, and storage of bodily exudates, such as a dusting layer, a transport layer, a wicking or acquisition/distribution layer, an intake layer, or a surge layer. See U.S. Pat. No. 4,798,603 issued Jan. 17, 1989, to Meyer et al., or a surge management layer, such as described in U.S. Pat. No. 5,486,166 issued Jan. 23, 1996, to Bishop et al., U.S. Pat. No. 5,364,382 issued Nov. 15, 1994, to Latimer et al., U.S. Pat. No. 5,490,846 to Ellis et al., U.S. Pat. No. 5,429,629 to Latimer et al., U.S. Pat. No. 5,509,915 to Hanson et al., U.S. Pat. No. 5,192,606 to Proxmire et al.

The bodyside liner 18 consists of a nonwoven or other soft material for contacting the wearer's skin. The bodyside liner 18 has an outer (exterior) surface 28 that faces toward the wearer and an inner (interior) surface 30 that faces away from the wearer. The bodyside liner 18 is described in more detail below. The bodyside liner 18 is compliant and soft feeling to the wearer. The bodyside liner 18 may be any soft, flexible, porous sheet that is aqueous liquid permeable, permitting aqueous liquids to readily penetrate into its thickness. A suitable bodyside liner 18 may be manufactured from a wide range of materials, such as natural fibers (e.g., wood or cotton fibers), synthetic fibers (e.g., polyester or polypropylene fibers) or from a combination of natural and synthetic fibers or reticulated foams and apertured plastic films.

The bodyside liner 18 is formed of an aqueous liquid permeable material so that aqueous liquid waste, and possibly semi-solid waste as well, can pass through to the absorbent core 14 and be absorbed by the absorbent core 14 of the absorbent article 10. A suitable bodyside liner 18 may be comprised of a nonwoven web, a spunbond, meltblown or bonded-carded web composed of synthetic polymer filaments or fibers, such as polypropylene, polyethylene, polyesters or the like, a perforated film, or a web or natural polymer filaments or fibers such as rayon or cotton.

In addition, the bodyside liner 18 may be treated with a surfactant to aid in aqueous liquid transfer. Suitably, the bodyside liner 18 is a nonwoven spunbond. Suitably, the spunbond material is available from Kimberly-Clark Corporation, located in Roswell, Ga. The bodyside liner 18 has a weight from about 0.3 oz. per square yard (osy) to about 2.0 osy and alternatively about 0.5 osy. The bodyside liner 18 of the underpant maybe printed, colored or decoratively embossed. The bodyside liner 18 can also be a nonwoven web or sheet of polyolefin fibers, such as polypropylene, polyester, polyethylene, Rayon, chisso and the like. The bodyside liner 18 may also be a plastic film with perforations, an expanded plastic webbing material or a scrim material. The bodyside liner 18 has a pore size that readily allows the passage therethrough of air, sweat, and perspiration due to the breathability of the material. The bodyside liner 18 may be selectively embossed or perforated with discrete slits or holes extending therethrough.

Ideally, the fabric of the bodyside liner 18 is surface treated with a surfactant such as that commercially available from Union Carbide Chemicals and Plastics Company, Inc., of Danbury, Conn., U.S.A. under the trade designation TRITON X-102. As used herein, the term "fabric" refers to all of the woven, knitted and nonwoven fibrous webs. The term "nonwoven web" means a web of material that is formed without the aid of a textile weaving or knitting process.

As an alternate material, an aqueous liquid permeable bodyside liner 18 can be made of a carded web of polyester fibers bonded to a spunbonded polypropylene or polyethylene carrier sheet. The carded material is made up of about 20 to about 60 weight percent polypropylene or polyethylene and about 80 to about 40 weight percent polyester. The basis weight of this material can be between about 30 gsm and about 70 gsm.

The back sheet member 12 is needed to prevent aqueous liquid strike through to the outer clothing when bodily fluid is discharged onto the absorbent core 14 of the absorbent article 10. The back sheet member 12 typically consists of an aqueous liquid impermeable film such as polyethylene. The aqueous liquid impermeable back sheet member 12 has an outer (exterior) surface 32 that faces away from the wearer and an inner (interior) surface 34 that faces toward the wearer. In construction of the disposable absorbent article 10, the back sheet member 12, acting as a barrier, should retard the movement of the aqueous liquid through the absorbent article 10 by making the back sheet member 12 resistant to penetration normally encountered under wearing conditions. The back sheet member 12 desirably comprises a material that is formed or treated to be aqueous liquid impermeable.

Alternatively, the back sheet member 12 may comprise an aqueous liquid permeable material and other suitable means (not shown), such as an aqueous liquid impermeable layer associated with the absorbent core 14 may be provided to impede aqueous liquid movement away from the absorbent core 14 of the absorbent article 10. The disposable absorbent article 10 may be rendered aqueous liquid impermeable by any method well known in the art such as coating the absorbent core 14 or by securing a separate aqueous liquid impermeable material to the absorbent core 14. The back sheet member 12 may comprise a thin, aqueous liquid impermeable web or sheet of plastic film such as polyethylene, polypropylene, polyvinyl chloride or similar material. Other acceptable materials include a single spunbonded layer of the above types of materials, two layers of spunbonded and meltblown materials or a three-layer material of spunbonded-meltblown-spunbonded material. Suitable foam materials may also be used, as well as materials that are both aqueous liquid impermeable and vapor-permeable.

Alternately, the back sheet member 12 may comprise a nonwoven, fibrous web which has been suitably constructed and arranged to have low aqueous liquid permeability. Still alternately, the back sheet member 12 may comprise a layered or laminated material, such as a thermally bonded plastic film and nonwoven web composite. Alternatively, the back sheet member 12 consists of a aqueous liquid impermeable film or foam which is permeable to water vapor under normal wearing conditions. More preferred, the back sheet member 12 has a water vapor transmission rate of at least about 800 grams/m$^2$/24 hours measured by ASTM E96-92. One example of a suitable film is a 39.4 grams per square meter microporous film produced by Mitsui and sold by Consolidated Thermoplastics (CT) under the tradename of ESPOIR® N-TAF-CT.

The absorbent articles 10 may also include elastic members 36 in the waist 42 (in absorbent articles 10 such as under pants and briefs), in the regions surrounding the leg openings 38 and 40, in the waist portions (not shown) as fit elastics (in absorbent articles 10 such as under pants), in side panels (not shown) (in absorbent articles 10 such as briefs and under pants), and in flap or barrier structures (not shown). The elastic members 36 may be in the form of strips, ribbons, connected ribbons or strips, sheets, strands, bands, threads, filaments, or any combination of these shapes and others known to the art. The elastic members 36 may also be of latent elastic material that is activated after placement in the absorbent articles 10.

The compositions of the present invention are solid or semisolid at 30° C. As used herein, the term "semisolid" refers to a composition having a rheology typical of pseudoplastic or plastic fluids. Because the compositions are in at as least a semisolid state at ambient temperatures, migration of the composition is minimized. The compositions, being solid or semisolid at ambient temperatures, do not have the tendency to migrate into the interior of the bodyside liner 18 or the tissue material 20 and ultimately into the absorbent article 10 to which the composition has been applied. The compositions are transferable to the wearer's skin by normal contact, movement of the wearer, or the body heat of the wearer.

The bodyside liner 18 or the tissue material 20 contains an effective amount of the composition of the present invention. As used herein, the term "bodyside liner" is used interchangeably with the term "tissue material". As used herein, the phrase "effective amount of the composition" refers to an amount of the composition which, when applied to a bodyside liner 18 or the tissue material 20, will be effective in reducing abrasion and irritation.

The composition is applied to the outer surface 28 of the bodyside liner 18 or the tissue material 20 of the absorbent article 10. Any of a variety of application methods that evenly distribute lubricious materials having a molten or liquid consistency can be used. Suitable methods include spraying, slot coating, printing (such as flexographic printing), coating (such as gravure coating), extrusion, or combinations of these methods, such as spraying the composition on a rotating surface, then transferring the composition to the outer surface 28 of the bodyside liner 18 or the tissue material 20.

The manner of applying the composition to the bodyside liner 18 or the tissue material 20 should be such that the bodyside liner 18 or the tissue material 20 does not become saturated with the composition. If the bodyside liner 18 or the tissue material 20 becomes saturated with the composition, the fluid permeability of the bodyside liner 18 or the tissue material 20 may be reduced or blocked. In addition, saturation of the bodyside liner 18 or the tissue material 20 is not necessary to obtain therapeutic or protective benefits from the composition of the present invention.

A variety of fastening means 44 can be used for securing the absorbent article 10 around or in contact with the wearer including tape fasteners, belts, ties, disposable and reusable garments, and mechanical type fasteners. The mechanical type fasteners include buttons, button holes, snaps, buckles, clasps, hooks and loops, end extensions, tabs, and the like which are designed or adapted to interlock or engage some type of a complimentary device or the outer cover of the absorbent article 10. Suitable engaging elements for such mechanical closure elements include self-engaging geometric shaped materials, such as hooks, loops, snaps, buckles, bulbs, mushrooms, arrowheads, balls on stems, male and female mating components, or the like. In addition, elasticized fasteners are also used in assuring better fit of such absorbent articles 10. Examples of some fastening systems and securement members are disclosed in U.S. Pat. No. 5,423,789 to Kuen; U.S. Pat. No. 5,405,342 to Roessler et al.; U.S. Pat. No. 5,403,302 to Roessler et al.; U.S. Pat. No. 5,399,219 to Roessler et al.; U.S. Pat. No. 5,386,595 to Kuen et al.; U.S. Pat. No. 5,374,262 to Keuhn, Jr. et al.; U.S. Pat. No. 5,318,555 to Siebers et al.; U.S. Pat. No. 5,304,162 to Kuen; U.S. Pat. No. 5,288,546 to Roessler et al.; U.S. Pat. No. 5,176,671 to Roessler et al.; U.S. Pat. No. 5,176,671 to Roessler et al.; and, U.S. Pat. No. 5,019,073 to Roessler et al.

The disposable absorbent articles 10 may also include flap or gasket structures (not shown). These flap or gasket structures can be assembled in a number of different configurations, including those disclosed in U.S. Pat. No. 4,704,116 issued to Enloe on Nov. 3, 1987, U.S. Pat. No. 4,846,823 issued to Enloe on Jul. 11, 1989, U.S. Pat. No. 5,413,570 issued to Enloe on May 9, 1995, U.S. Pat. No. 5,415,644 issued to Enloe on May 16, 1995 and U.S. Pat. No. 5,599,338 issued to Enloe on Feb. 4, 1997.

The compositions of the present invention may be applied to the entire outer surface 28 of the bodyside liner 18 or the tissue material 20 or portions thereof. Preferably, the composition is applied in a stripe or pattern aligned with a centered on the longitudinal centerline 46 of the disposable absorbent article 10. (See FIG. 1.) The dimensions of the stripe or pattern will vary with the different absorbent articles 10 to which the composition is being applied.

The compositions of the present invention may be applied non-uniformly to the outer surface 28 of the bodyside liner 18 or the tissue material 20. The term "non-uniformly", as used herein, refers to the amount, pattern of distribution, thickness of the application, or the like, of the composition can be varied over the outer surface 28 of the bodyside liner 18 or the tissue material 20. The composition could be applied to the inner surface 30 of the bodyside liner 18 or the tissue material 20, alone or in combination with the application of the composition to the outer surface 28.

The compositions of the present invention can be applied to the bodyside liner 18 or the tissue material 20 at any point during assembly of the absorbent article 10. For example, the raw material web being formed into the bodyside liner 18 or the tissue material 20 may be treated with the composition before the web is processed into the bodyside liner 18 or the tissue material 20; the bodyside liner 18 or the tissue material 20 may be treated with the composition before being incorporated into the absorbent article 10; and, the bodyside liner 18 or the tissue material 20 may be treated with the composition after the bodyside liner 18 or the tissue material 20 has been incorporated into the absorbent article 10.

EXAMPLES

The following examples are presented to provide a more detailed understanding of the invention. The particular materials and parameters are exemplary and are not intended to limit the scope of the invention.

The following formulas are used in Examples 1–3.

|  | weight percent |
|---|---|
| Formula 1 | |
| Petrolatum | 93.7% |
| Glycerin | 5% |
| PROLIPID 141 | 1.0% |
| (International Specialty Products, Wayne, NJ) | |
| Tocopherol acetate | 0.3% |
| Formula 2 | |
| Petrolatum | 88.7% |
| Glycerin | 5% |
| PROLIPID 141 | 1.0% |
| (International Specialty Products, Wayne, NJ) | |
| Tocopherol acetate | 0.3% |
| Avocadin (CRODA) | 5.0% |
| Formula 3 | |
| Petrolatum | 83.7% |
| Glycerin | 5% |
| Tocopherol acetate | 0.3% |
| Sunflower oil | 9.2% |
| Soy sterol | 0.8% |
| PROLIPID 141 (ISP) | 1.0% |
| (International Specialty Products, Wayne, NJ) | |
| Formula 4 | |
| Petrolatum | 100% |
| Formula 5 | |
| Petrolatum | 85.4% |
| Glycerin | 5% |
| Glyceryl monoleate | 3% |
| Borage oil | 3% |
| Soy sterol | 3% |
| Aloe | 0.3% |
| Tocopherol acetate | 0.3% |
| Formula 6 | |
| Petrolatum | 86.4 |
| Glycerin | 5% |
| Glyceryl monoleate | 3% |
| Borage oil | 3% |
| Soy sterol | 1% |
| PROLIPID 141(ISP) | 1.0% |
| (International Specialty Products, Wayne, NJ) | |
| Aloe | 0.3% |
| Tocopherol acetate | 0.3% |

-continued

| | weight percent |
|---|---|
| Formula 7 | |
| 1) Glycerin | 5.00 |
| 2) Prolipid 141 | 1.00 |
| 3) Soya Sterol | 0.80 |
| 4) Sunflower Oil | 10.00 |
| 5) Petrolatum USP | 43.20 |
| 6) Allyson Wax AE-1692 | 40.00 |
| Formula 8 | |
| 1) Petrolatum USP | 60.00 |
| 2) Allyson Wax AE-1692 | 38.90 |
| 3) Butyl paraben | 0.20 |
| Formula 9 | |
| 1) Petrolatum USP | 60.00 |
| 2) Stearyl Alcohol | 40.00 |

Example 1

Lipid-enriched formulations for treatment of absorbent articles promote barrier repair as measured by TEWL.

All studies were conducted in a temperature and humidity controlled room (71°±5° F.; 40%±5% relative humidity).

Transepidermal Water Loss (TEWL)

The volar forearm of 24 panelists were abraded by an emery cloth to increase TEWL levels to 18–20 g/m$^2$/hr. After abrasion, fifteen microliters of a hydrophobic lipid-enriched formulation was topically applied to the volar forearm. TEWL measurements were obtained using a Dermalab evaporimeter instrument at 1, 2, and 4 hours. Mean TEWL values are expressed in Table 1. Repeated measures ANOVA was used to adjust for the repeated TEWL measures.

TABLE 1

TEWL (g/m$^2$/hr) Results- Lipid-enriched absorbent article formulations

| | PIR Mean | 1 Hour Mean | 2 Hour Mean | 4 Hour Mean |
|---|---|---|---|---|
| Formula 1 | 19.8 | 6.6 * | 6.6 * | 79 * |
| Formula 2 | 18.3 | 6.4 * | 6.6 * | 73 * |
| Formula 3 | 19.2 | 6.5 * | 6.5 * | 71 * |
| Untreated | 19.2 | 15.2 | 14.3 | 14.3 |

* denotes significantly different than untreated site.

The above data clearly demonstrates that the lipid-enriched formulations improve skin barrier repair.

Example 2

Lipid-enriched formulations for treatment of absorbent articles enhance skin moisturization as measured by conductance.

All studies were conducted in a temperature and humidity controlled room (71°±5° F.; 40%±5% relative humidity).

Conductance

Fifteen microliters of a hydrophobic lipid-enriched formulation for an absorbent article was topically applied to the volar forearm. Conductance measurements were obtained using the Skicon instrument at 1, 2, 4, and 6 hours. Mean conductance values are expressed in Table 2. A pair-wise comparison for each time period using univariate ANOVAs was applied.

TABLE 2

Conductance-Lipid-enriched formulations for absorbent articles

| | Baseline Mean | 1 Hour Mean | 2 Hour Mean | 4 Hour Mean | 6 Hour Mean |
|---|---|---|---|---|---|
| Formula 1 | 202 | 370* | 357* | 335* | 310* |
| Formula 2 | 220 | 344* | 349* | 333* | 319* |
| Formula 3 | 220 | 342* | 340* | 333* | 320* |
| Untreated | 200 | 220 | 235 | 232 | 223 |

*denotes significantly different than untreated site.

The above data clearly demonstrates that the lipid-enriched formulations improve skin barrier moisturization.

Example 3

Lipid-enriched formulations for treatment of absorbent articles enhance skin moisturization as measured by conductance.

All studies were conducted in a temperature and humidity controlled room (71°±5° F.; 40%±5% relative humidity).

Conductance

Fifteen microliters of lipid-enriched formulation for an absorbent article was topically applied to the volar forearm. Conductance measurements were obtained at 1, 2, 4, and 6 hours. Mean conductance values for the baseline, 4, and 6 hour timepoints are expressed in Table 3. A pair-wise comparison for each time period using univariate ANOVAs was applied.

TABLE 3

Conductance-Lipid-enriched formulations for an absorbent article

| | Baseline Mean | 4 Hour Mean | 6 Hour Mean |
|---|---|---|---|
| Formula 4 | 187 | 243 | 247 |
| Formula 5 | 179 | 281* | 289* |
| Formula 6 | 195 | 295* | 297* |
| Untreated | 194 | 210 | 215 |

*denotes significantly different than untreated site.

The above data clearly demonstrates that the lipid-enriched formulations improve skin barrier moisturization.

Example 4

Lipid-enriched liners enhance skin barrier as measured by transepidermal water loss (TEWL) and exclusion of water-soluble insult.

All studies were conducted in a temperature and humidity controlled room (71° F.±5° F.; 40±5% relative humidity). Prior to the start of the study, the volar forearms of 20 panelists were washed to remove any endogenous surface oils. Briefly, each arm was lathered using Ivory soap for 30 seconds. The lather remained on the arm for 90 seconds before a through rinsing. The arms were patted dry and a twenty minute wait period was required prior to obtaining baseline TEWL and chromameter readings.

The study included four test products and an untreated control site. The test products included liners treated with formulas 7, 8, 9, or an untreated liner. The add on level of treatment to each liner was approximately 0.2 g treatment/ liner.

TEWL

After obtaining a baseline TEWL measurement using a Dermalab evaporimeter instrument, the forearm was wiped with a folded liner. The liner was folded in half lengthwise and wiped across the arm site 5 times, opened, then refolded to expose a new surface and again wiped 5 times. All wipings were done with the treated side of the liner. This procedure was repeated every 15 minutes for a total of 30 cycles. TEWL and chromameter reading were taken after the last cycle. Least square of the mean of the last TEWL reading with baseline values subtracted are expressed in Table 4. TEWL values were found to decrease due to recovery of the barrier after the washout as well as due to deposition of the lotion treatment. Significant differences were found between the means of the codes.

TABLE 4

TEWL (g/m2/hr) Results-Lipid enriched liner

|  | TEWL |
|---|---|
| Untreated, control site | −0.69 |
| Untreated liner | −0.60 |
| Liner treated with formula 7 | −1.28* |
| Liner treated with formula 8 | −0.92 |
| Liner treated with formula 9 | −0.97 |

*denotes significantly different than liner and control sites.

The above data clearly demonstrates that liners treated with lipid-enriched formulations improve skin barrier function after repetitive wiping.

Chromameter

The wiped skin sites were then challenged with a water soluble dye (0.5% methylene blue) by adding 300 microliters of the dye to a HillTop chamber. A chamber was placed on each site and pressed down gently to ensure contact with the skin. After 1 minute of contact the chamber was removed and the arm rinsed under water for 30 seconds. Each site was blotted dry and a chromameter reading was obtained. A control site was included on one arm for the ability to determine the extent of dye uptake on untreated skin. The chromameter readings were recorded in the L, a, b scale. L is luminosity, a is red/green (positive values=red), and b is yellow/blue (positive values=yellow). Since the b value is most relevant for a methylene blue dye uptake study, only this data was analyzed in detail. The results are expressed in Table 5 as the least square of the mean with the post wiping baseline readings subtracted out.

TABLE 5

Chromameter Results-Lipid enriched liner

|  | b value |
|---|---|
| Untreated, control site | −18.11 |
| Untreated liner | −21.13** |
| Liner treated with formula 7 | −12.63* |
| Liner treated with formula 8 | −18.93 |
| Liner treated with formula 9 | −18.78 |

*denotes significantly lower dye uptake than all other treatments (p value <0.001).
**denotes significantly higher dye uptake than all other treatments (p value <0.01).

The above data clearly demonstrates that liner with lipid-enriched formulations prevent uptake of methylene blue dye significantly better than all other treatments indicating protection against water soluble materials.

Thus, the Examples representatively illustrate that the lipid-enriched hydrophobic composition of the present invention may provide absorbent articles having improved softness as well as providing improved protection of the skin barrier function. Accordingly, the different aspects of the present invention can advantageously provide absorbent articles which, when compared to conventional absorbent articles, are softer and have improved protection of skin barrier function. Such absorbent articles can advantageously be used for diapers, training pants, adult incontinence products, underpants, and feminine care products and the like.

While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

We claim:

1. A body facing material having an outer surface, wherein the outer surface of said material has a composition that enhances skin barrier comprising:
  from about 0.1 to about 50 weight percent of natural fats or oils containing linolenic acid or palmitic acid and derivatives thereof;
  from about 0.1 to about 10 weight percent of sterols or sterol derivatives;
  from about 1 to about 20 weight percent of water-in-oil emulsifying surfactant with an HLB range from about 3 to about 6;
  from about 1 to about 15 weight percent of a water soluble or water dispersible humectant;
  from about 5 to about 95 weight percent of emollient;
  from about 5 to about 95 weight percent of wax; and,
  from about 1 to about 25 weight percent of oil soluble or oil dispersible viscosity enhancer,
wherein said composition having a melting point from about 30° C. to about 100° C., a process viscosity of greater than about 50 centipoise, and a penetration hardness of from about 5 millimeters to about 360 millimeters.

2. The material of claim 1, wherein said natural fats or oils are selected from the group consisting of: avocado oil; borage seed oil; canola oil; cottonseed oil; evening primrose oil; lanolin and lanolin derivatives; palm oil; soybean oil; sunflower seed oil; sweet almond oil; linolenic acid; palmitic acid; stearic acid; [PROLIPID 141] a mixture of between about 3 to about 40% lecithin, between about 15 to about 30% glyceryl monostearate, between about 15 to about 40% blend of palmitic and stearic acid, and between about 0 to about 30% maleated soybean oil; and mixtures thereof.

3. The material of claim 1, wherein said humectant is selected from the group consisting of glycerin; hydrogenated starch hydrolysate; propylene glycol; sodium PCA; sodium lactate; sorbitol; and mixtures thereof.

4. The material of claim 1, wherein said viscosity enhancer is selected from the group consisting of polyolefin resins; polyolefin polymers; ethylene/vinyl acetate copolymers; polyethylene; and mixtures thereof.

5. The material of claim 1, wherein said sterol or sterol derivative is selected from the group consisting of soy sterol; cholesterol; lanasterol; and mixtures thereof.

6. The material of claim 1, wherein said emulsifying surfactant is selected from the group consisting of sorbitan oleate; glyceryl stearate; sorbitan stearate; and mixtures thereof.

7. The material of claim 1, wherein said emollient is selected from the group consisting of petrolatum; mineral oil; cosmetic esters; and mixtures thereof.

8. The material of claim 1, wherein said wax is selected from the group consisting of ozokerite; cerasin; microcrystalline wax; and mixtures thereof.

9. The material of claim 1, wherein the add-on amount of said composition is from about 0.1 grams per meter squared (g/m$^2$) to about 30 g/m$^2$ of said material.

10. A method for enhancing/restoring/maintaining skin barrier function skin of a user, comprising the steps of:
   a) contacting a body facing material on said skin of said user wherein said material comprises a skin barrier enhancing/restoring/maintaining composition that provides a skin barrier enhancing/restoring/maintaining benefit upon transfer of said composition to said user's skin;
   b) transferring at least a portion of said composition during use of said body facing material; and,
   c) repeating steps a) and b) with one or more additional body facing material with sufficient frequency to enhance/restore/maintain said skin barrier in an area of skin contacted by said body facing material, relative to skin contacted by an equivalent body facing material that does not comprise said skin barrier enhancing/restoring/maintaining composition,
   wherein said skin barrier enhancing/restoring/maintaining composition comprises:
      from about 0.1 to about 50 weight percent of natural fats or oils containing linolenic acid or palmitic acid and derivatives thereof, from about 0.1 to about 10 weight percent of sterols and sterol derivatives, from about 1 to about 20 weight percent of water-in-oil emulsifying surfactant having an HLB range from about 3 to about 6, from about 0.5 to about 10 weight percent of a water soluble or water dispersible humectant, from about 5 to about 95 weight percent of emollient, from about 5 to about 95 weight percent of wax, and from about 1 to about 25 weight percent of oil soluble or oil dispersible viscosity enhancer, wherein said composition having a melting point from about 30° C. to about 100° C., a process viscosity of greater than about 50 centipoise, and a penetration hardness of from about 5 millimeters to about 360 millimeters.

11. The method of claim 10, wherein said natural fats or oils are selected from the group consisting of: avocado oil; borage seed oil; canola oil; cottonseed oil; evening primrose oil; lanolin and lanolin derivatives; palm oil; soybean oil; sunflower seed oil; sweet almond oil; linolenic acid; palmitic acid; stearic acid; [PROLIPID 141] a mixture of between about 3 to about 40% lecithin, between about 15 to about 30% glyceryl monostearate, between about 15 to about 40% blend of palmitic and stearic acid, and between about 0 to about 30% maleated soybean oil; and, mixtures thereof.

12. The method of claim 10, wherein said sterol or sterol derivative is selected from the group consisting of soy sterol; cholesterol; lanasterol; and mixtures thereof.

13. The method of claim 10, wherein said humectant is selected from the group consisting of glycerin; hydrogenated starch hydrolysate; propylene glycol; sodium PCA; sodium lactate; sorbitol; and mixtures thereof.

14. The method of claim 10, wherein said viscosity enhancer is selected from the group consisting of polyolefin resins; polyolefin polymers; ethylene/vinyl acetate copolymers; polyethylene; and mixtures thereof.

15. The method of claim 10, wherein said body facing material comprising said skin-barrier enhancing/restoring/maintaining composition are used by said user on each use occasion.

16. The method of claim 10, wherein said body facing material which do not comprise a skin-barrier enhancing/restoring/maintaining composition are used by said user intermittently.

17. The method of claim 10, wherein said body facing material comprising said skin-barrier enhancing/restoring/maintaining composition are used by a user whose skin is compromised and are used with sufficient frequency to improve skin-barrier function.

* * * * *